United States Patent
Kneuer et al.

(10) Patent No.: US 8,606,600 B2
(45) Date of Patent: *Dec. 10, 2013

(54) METHOD AND APPARATUS FOR CONTROLLING A WARMING THERAPY DEVICE

(71) Applicant: Draeger Medical Systems, Inc., Telford, PA (US)

(72) Inventors: Harald Kneuer, Ambler, PA (US); Thorsten Waloschek, Flemington, NJ (US); Peter Medico, Breinigsville, PA (US); John Richards, Warrington, PA (US); Ines Poggensee, Heilshoop (DE); Nancy Files, Perkasie, PA (US); Philip Moehring, Luebeck (DE)

(73) Assignee: Draeger Medical Systems, Inc., Telford, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/851,505

(22) Filed: Mar. 27, 2013

(65) Prior Publication Data

US 2013/0217981 A1 Aug. 22, 2013

Related U.S. Application Data

(62) Division of application No. 12/271,225, filed on Nov. 14, 2008, now Pat. No. 8,442,843.

(60) Provisional application No. 61/005,510, filed on Dec. 5, 2007.

(51) Int. Cl.
*G06Q 50/00* (2012.01)

(52) U.S. Cl.
USPC .......................................................... 705/2

(58) Field of Classification Search
USPC ............................................................. 705/2
See application file for complete search history.

(56) References Cited

U.S. PATENT DOCUMENTS

| | | | |
|---|---|---|---|
| 4,161,172 A | 7/1979 | Pickering | 128/1 |
| 5,742,920 A | 4/1998 | Cannuscio et al. | 701/102 |
| 6,409,654 B1 | 6/2002 | McClain | 600/22 |
| 2002/0111386 A1 | 8/2002 | Sekins et al. | 514/759 |
| 2002/0196141 A1 | 12/2002 | Boone et al. | 340/540 |
| 2003/0176902 A1 | 9/2003 | Gunn et al. | 607/104 |
| 2004/0193096 A1 | 9/2004 | Cooper | 604/19 |
| 2007/0257018 A1 | 11/2007 | Huang | 219/217 |

FOREIGN PATENT DOCUMENTS

| | | | | |
|---|---|---|---|---|
| DE | 2259496 | 7/1973 | | A61B 7/00 |
| DE | 2740305 | 3/1979 | | A61G 3/00 |
| DE | 3216273 | 11/1983 | | A61B 5/11 |
| DE | 9402602.5 | 9/1994 | | A61G 11/00 |
| DE | 68927054 | 5/1998 | | A61B 5/087 |
| DE | 69612791 | 10/2001 | | A61G 11/00 |
| DE | 20114157 | 3/2002 | | A61G 11/00 |
| DE | 69634572 | 2/2006 | | A61M 1/36 |

(Continued)

OTHER PUBLICATIONS

German Search Report dated Jan. 13, 2010.

*Primary Examiner* — John Pauls
(74) *Attorney, Agent, or Firm* — DLA Piper LLP (US)

(57) ABSTRACT

An apparatus and method for controlling a warming therapy device (e.g., incubator, warmer, etc.) is described. In one exemplary embodiment, the apparatus includes a Graphical User Interface (GUI) coupled to the warming therapy device for monitoring patient medical information, and for controlling various aspects of the warming therapy device accordingly.

19 Claims, 8 Drawing Sheets

(56) References Cited

FOREIGN PATENT DOCUMENTS

| | | | | |
|---|---|---|---|---|
| DE | 60021626 | 5/2006 | ............... | A61F 7/10 |
| DE | 102005044434 | 8/2006 | ............ | A61G 11/00 |
| DE | 69837501 | 9/2007 | ............ | A61G 11/00 |
| DE | 202007010052 | 11/2007 | ............. | A61B 19/00 |
| DE | 602004006684 | 1/2008 | ............ | A61G 11/00 |
| DE | 102007057884 | 6/2008 | ................ | G06T 1/00 |
| EP | 2036496 | 3/2009 | ............. | A61B 5/113 |
| GB | 2436875 | 10/2007 | ............ | A61B 5/055 |
| JP | 11-137618 | 5/1999 | ............ | A61G 11/00 |
| WO | 2005/050523 | 6/2005 | ............. | G06F 19/00 |
| WO | 2005/050524 | 6/2005 | ............. | G06F 19/00 |

1

METHOD AND APPARATUS FOR CONTROLLING A WARMING THERAPY DEVICE

FIELD OF THE INVENTION

The present invention relates generally to a method and apparatus for controlling a warming therapy device (e.g., incubator, warmer, etc.). More particularly, the present invention relates to a method and apparatus for monitoring the conditions of a medical patient disposed on a warming therapy device, and controlling various aspects of the warming therapy device associated therewith.

BACKGROUND OF THE INVENTION

Infant care units, such as warming therapy devices (e.g., incubators, warmers, etc.) that includes various systems for controlling the temperature and humidity to facilitate the development of a premature infant, are known. Such devices conventionally include an infant support surface for supporting an infant, as well as means of protecting the infant, such as a hood or canopy which covers the infant support surface.

In some cases, conventional warming therapy devices include control panels for monitoring the status of the infant, and for controlling various aspects of the device (e.g., temperature, air flow, humidity, etc.). Such control panels typically comprise an Light Emitting Diode (LED) or Liquid Crystal Display (LCD) type displays, which convey only alphanumeric information (e.g., temperature values, humidity values), and are often time not intuitive to first time users. Conventional control panels for warming therapy devices do not include detailed display monitors (such as computer-type displays), touch-screen displays, or other features common in the field of computers.

Accordingly, there is presently a need for an apparatus for monitoring and controlling a warming therapy device which is intuitive and suitable for an infant patient environment.

SUMMARY OF THE INVENTION

An exemplary embodiment of the present invention comprises an apparatus including a warming therapy device and at least one monitor coupled to the warming therapy device for displaying information related to a medical patient, wherein the monitor operates to display at least one medical patient temperature level, and at least one resuscitation indicator on a single display screen.

An exemplary embodiment of the present invention also comprises a touch screen apparatus including a first display portion for displaying a first set of information related to a medical patient, a second display portion for displaying menu information, and a third display portion for displaying a second set of information related to a medical patient.

An exemplary embodiment of the present invention also comprises a method for monitoring a medical patient, including, displaying a first set of information related to a medical patient on a first portion of a computer monitor, displaying menu information on a second portion of a computer monitor, and displaying a second set of information related to a medical patient on a third portion of a computer monitor.

An exemplary embodiment of the present invention also comprises a computer system including at least one monitor, at least one processor, and at least one memory coupled to the at least one processor, wherein the at least one memory includes at least one program stored thereon, the at least one program being capable of performing the steps of displaying a first set of information related to a medical patient on a first portion of the at least one monitor, displaying menu information on a second portion of the at least one monitor, and displaying a second set of information related to a medical patient on a third portion of the at least one monitor.

An exemplary embodiment of the present invention also comprises a computer readable medium having embodied therein a computer program for processing by a machine, the computer program including a first code segment for displaying a first set of information related to a medical patient on a first portion of a computer monitor, a second code segment for displaying menu information on a second portion of the computer monitor, and a third code segment for displaying a second set of information related to a medical patient on a third portion of the computer monitor.

An exemplary embodiment of the present invention also comprises a computer monitor apparatus including a first display portion for displaying an image representative of a medical patient, a second display portion for displaying a first set of information related to a medical patient, wherein the second display portion comprises a substantially circular display which substantially surrounds the first display portion.

An exemplary embodiment of the present invention also comprises an apparatus including a warming therapy device, and at least one monitor coupled to the warming therapy device for displaying information related to a medical patient, wherein the monitor operates to display at least one medical patient temperature level, and at least one CPAP indicator on a single display screen.

DETAILED DESCRIPTION

Figure 1:
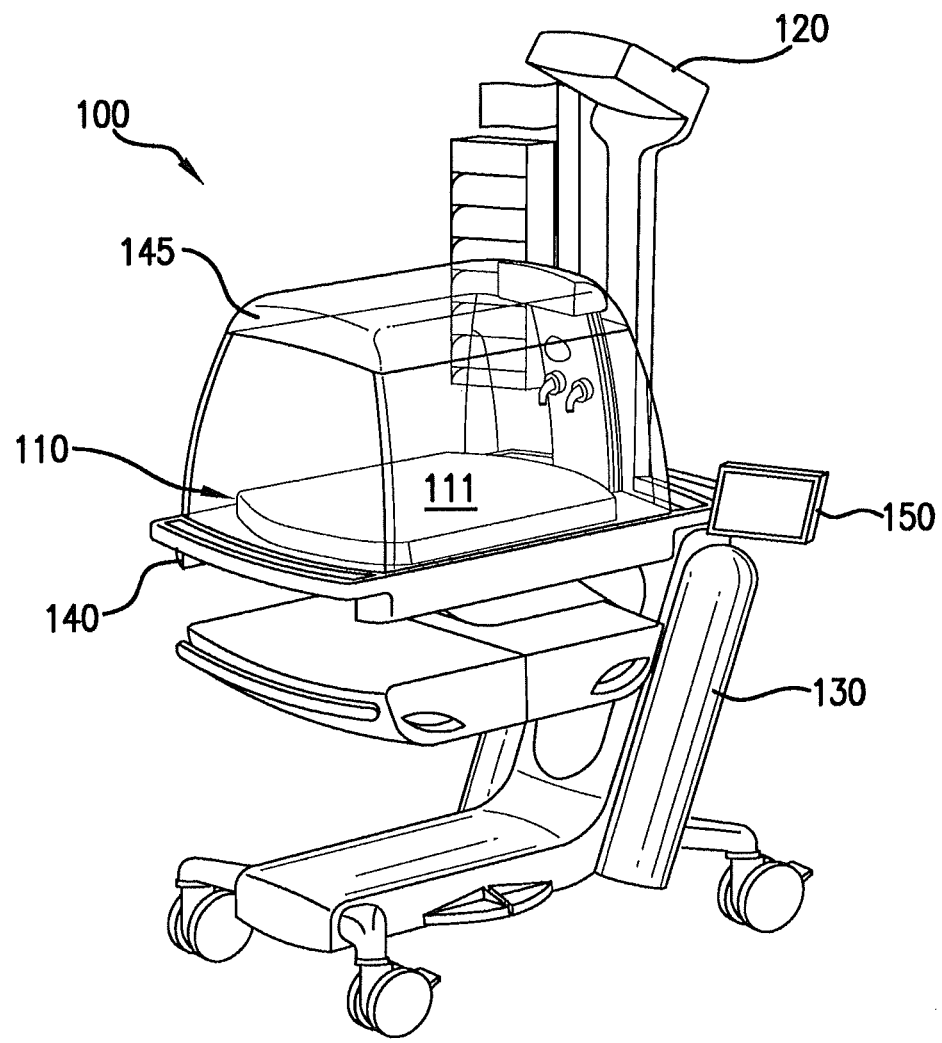
FIG. 1 is perspective view of a warming therapy device according to a first exemplary embodiment of the present invention.

The present invention relates generally to a method and apparatus for controlling a warming therapy device (e.g., incubator, warmer, etc.), and in particular to an interface for displaying various conditions of a medical patient disposed on the warming therapy device, and for permitting control of various medical monitors and devices. As described below, the interface may comprise a touch screen Graphical User Interface (GUI) in certain exemplary embodiments.

The GUI presents a completely new holistic approach to the control and monitoring of an infant patient disposed on or in the warming therapy device. In certain exemplary embodiments, the GUI may comprise a full-color touch screen display which allows for customization of the displayed information according to the user's needs. For example the arrangement of data on the GUI may follow the current medical application, which can include, but is not limited to, processes such as thermo-regulation (i.e., temperature control), thermo-monitoring (i.e., temperature monitoring), phototherapy, respiratory support, resuscitation, noise control, audio stimulation, weighing, etc. Short and long-term trends may also be displayed on the GUI, and combined for further analysis. The GUI may also include a series of alarms, as well as an alarm log, which may be combined with the short and long-term trend information for analysis, and future prevention of similar events.

The GUI is intended to represent a patient and the patient's environment on the GUI, and to place the measured values and indicators relating to the patient and the patient's environment at locations on the GUI that correspond to their physical location. For example, a mattress temperature value may be represented on a bottom portion of the GUI (under the representation of the patient), which corresponds to the location of the mattress in the warming therapy device relative to the patient. One goal of the present invention is to make the use of the GUI more intuitive to first time users, and more effective to repeat users. Another goal is to make the GUI better suited for a infant patient environment (e.g., Neonatal Intensive Care Unit (NICU)) in that its appearance is less foreign (and less threatening) to visiting parents, while still remaining effective and professional.

The following abbreviations are used herein, and are defined as follows:
bpm—beats per minute, unit for pulse rate.
CPAP—Continuous Positive Airway Pressure; used to keep airways open.
FiO2—Fractional Inspired O2 concentration.
GUI—Graphical User Interface.
KPa—KiloPascals, Unit of pressure (1 KPa=0.145038 PSI).
LPM—Liters Per Minute, Unit of gas flow.
MIB—Medical Information Bus.
nCPAP—Nasal CPAP.
NICU—Neonatal Intensive Care Unit.
PEEP—Positive End Expiratory Pressure; pressure applied to the patient airway during expiration.
PIP—Peak Inspiratory Pressure; the pressure limit of the gas possible to deliver.
PSI—Pounds per Square Inch; unit of gas pressure (1 PSI=6.8947 KPa).
Trendelenburg—a position in which a patient's body is laid flat on the back with the head lower than the pelvis.

FIG. 1 shows a warming therapy device (e.g., incubator, warmer, etc.) 100 according to a first exemplary embodiment of the present invention. The warming therapy device 100 includes a radiant heater head 120, a patient support assembly 130, and a mattress tray assembly 140. The mattress tray assembly 140 may also include a hood 145, and a mattress tray 110, with a mattress 111 disposed therein. Additionally, the warming therapy device 100 may include at least one computer monitor 150 for displaying various information associated with a patient disposed on the warming therapy device. The computer monitor may be coupled to the patient support assembly 130 of the warming therapy device 100 in either a wired or wireless manner. If the computer monitor 150 is wirelessly coupled to the patient support assembly 130, a caregiver can remove the monitor from the assembly and move around with it within a wireless coverage zone. In such an embodiment, the monitor 150 would preferably include a rechargeable internal battery which would provide power during wireless use. Similarly, the patient support assembly 130 would preferably include a charging unit for the internal battery, to charge the monitor 150 when it is stationed on the assembly. Although the computer monitor 150 is shown as being coupled to the patient support assembly 130 in FIG. 1, those of ordinary skill in the art will realize that the computer monitor may be coupled to any suitable portion of the warming therapy device 100, or may be coupled to a separate unit entirely, without departing from the scope of the present invention.

Figure 2:
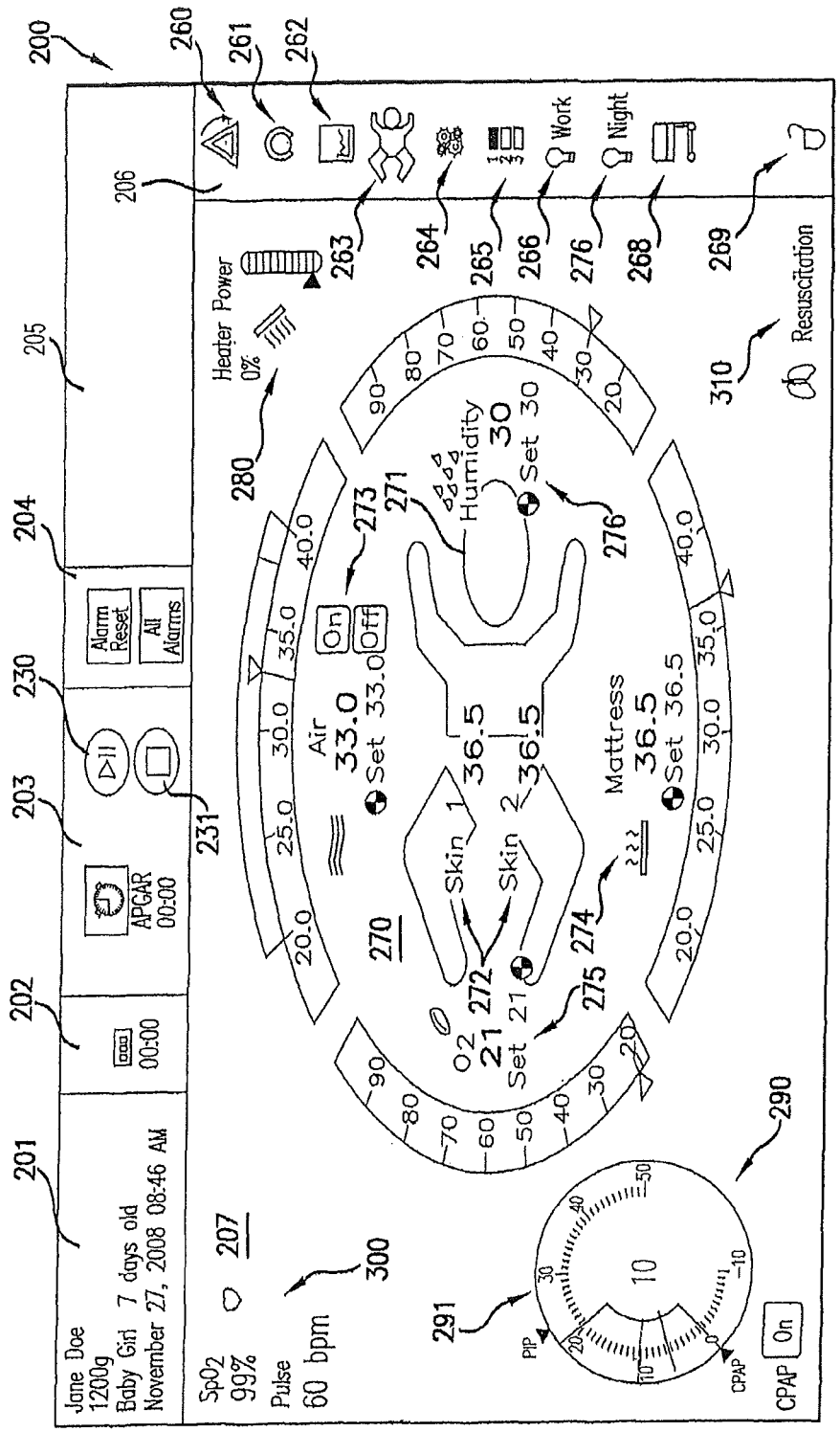
FIG. 2 is front view of a computer monitor associated with the warming therapy device shown in FIG. 1, showing a touch screen Graphical User Interface (GUI) according to a first exemplary embodiment of the present invention.

FIG. 2 shows a Graphical User Interface (GUI) 200 according to a first exemplary embodiment of the present invention which may be displayed on the monitor 150 discussed above. In the first exemplary embodiment, the GUI 200 comprises a 'touch screen' (as is known in the art) which is capable of receiving input from a user (e.g., caregiver) by the user touching various portions of a monitor (e.g., monitor 150) associated with the GUI. The GUI 200 includes a patient information portion 201, which can display various personal information associated with the patient, such as name, weight, sex, and age. The patient information portion 201 can also display the current date and time for reference purposes. The GUI 200 also includes a battery indicator portion 202 which shows the charge level of the internal battery. The battery indicator portion 202 is important when the caregiver is operating the monitor 150 wirelessly (as described above), as it indicates when the monitor must be placed back on the patient support assembly for recharge.

The GUI 200 also includes an APGAR portion 203 for assisting the caregiver in performing an APGAR examination. The APGAR portion 203 includes a timer which may be started or stopped by selection of the 'play/pause' radio button, and which may be reset by selection of the 'reset' radio button 231. Preferably, an audible alarm sounds at 1, 5 and 10 minute intervals during the APGAR examination.

The GUI 200 also includes an alarm control portion 204 for controlling various alarms. The alarm control portion 204 includes an 'Alarm Reset' radio button 240, which, when selected, resets all the alarms controlled from the GUI 200. The alarm control portion 204 includes an 'All Alarms' radio button 241, which, when selected, displays an additional dialog box or window (not shown) with a description of all the alarms controlled from the GUI 200. The GUI 200 also includes an alarm display portion 205 for displaying an indicator of one or more alarms. For example, if the patient's FiO2 is low, the alarm display portion 205 will display the text "FiO2 Low" and so forth.

The GUI 200 also includes a main menu portion 206 for allowing the caregiver to perform various functions. The main menu portion 206 includes an Alarm icon 260, a Therapy Settings icon 261, a Trends/Review icon 262, a Procedures icon 263, a System Setup icon 264, a View icon 265, a Work Light icon 266, a Night Light icon 267, a Bed Adjustment icon 268, and a Screen Lock icon 269. Although not shown in FIG. 2, the main menu portion 206 may include additional icons for performing additional functions, such as, a Hood icon for opening and closing the hood 145, a Tilt icon for tilting the mattress tray assembly 140, and a Help icon for accessing help information for the GUI.

If the caregiver selects the Alarm icon 260, a separate dialog box or window is displayed (not shown) which allows the caregiver to manipulate the alarm settings (e.g., which alarms are active, audio options, etc.). This dialog box (and all the other dialog boxes described below) may be configured to disappear or be removed from the GUI 200 if there is no activity in the GUI for a certain period of time (e.g., 5 seconds). Controls available from the Alarm dialog box may include radio buttons, softkeys or other equivalent means for controlling various alarms related to conditions such as patient temperature, mattress temperature, oxygen levels, humidity levels, etc. The Alarm dialog box may also permit the disabling of all alarms, the display of all current alarms and alarm levels, the display of historical alarms and alarm levels and alarm volume controls.

If the caregiver selects the Therapy Settings icon 261, a separate dialog box or window is displayed (not shown) which allows the caregiver to manipulate the therapy settings (e.g., mattress heating, heated air circulation, resuscitation settings, etc.). Controls available from the Therapy Settings dialog box may include radio buttons, softkeys or other equivalent means for controlling temperature, air flow and humidity within the warming therapy device, mattress temperature, radiant heater temperature, oxygen levels, resuscitation processes, and nCPAP processes. The Therapy Settings dialog box may also permit the enabling or disabling of a Kangaroo Mode®, wherein a parent or caregiver removes the medical patient from the warming therapy device but remains in close proximity.

If the caregiver selects the Trends/Review icon 262, a separate dialog box or window is displayed (not shown) which allows the caregiver to manipulate the trends and review settings (e.g., select trends to monitor, display trends, display current values, etc.). Controls available from the Trends/Review dialog box may include radio buttons, softkeys or other equivalent means for displaying various trends.

If the caregiver selects the Procedures icon 263, a separate dialog box or window is displayed (not shown) which allows the caregiver to manipulate the procedures settings (e.g., weight measurements, phototherapy procedures, etc.). Controls available from the Procedures dialog box may include radio buttons, softkeys or other equivalent means for performing various procedures such as weighing the patient, performing phototherapy on the patient (to reduce or eliminate bilirubin), and performing audio stimulation (e.g., playing music or soothing sounds for the patient). The Procedures dialog box may also permit the setting of various timers for the above-referenced procedures.

If the caregiver selects the System Setup icon 264, a separate dialog box or window is displayed (not shown) which allows the caregiver to manipulate the system settings (e.g., screen settings, trend settings, view settings, color settings, alarm settings, etc.). Controls available from the System Setup dialog box may include radio buttons, softkeys or other equivalent means for controlling current date and time, language, display brightness, display and editing of patient demographic information, enabling or disabling APGAR displays and controls, setting of units of measurement (e.g., ounces, pounds, kilograms, etc.), enabling or disabling locking of the touch screen, and enabling or disabling tilt and height adjustment controls. The System Setup dialog box may also permit control of trend default levels (e.g., for display in the Trends/Review dialog box), defaults views (e.g., for display in the View dialog box), default alarms and levels (e.g., for display in the Alarm dialog box), and default therapies and levels (e.g., for display in the Therapy Settings dialog box). The System Setup dialog box may also permit the assignment of various colors to different parameters, to make on-screen identification easier. For example, the caregiver may assign the color red to a patient temperature display, and the color blue to an oxygen level display. The System Setup dialog box may also permit the saving of data to an external data storage medium (e.g., Universal Serial Bus (USB) Drive, or the like), and the loading of data from an external data storage medium. The System Setup dialog box may also permit calibration of the oxygen sensors.

If the caregiver selects the View icon 265, the view setting is changed. Each time the user select the View icon 265, the view setting is changed as between three (3) different views. These views may comprise: (1) a Portrait View (7.2-8.4 inches wide by 9.6-11.2 inches high), (2) a Landscape View (9.6-11.2 inches wide by 7.2-8.4 inches high), and (3) a Split Screen View (two screens side by side with each being 4.5 inches wide by 3.25 inches high). In this manner, the caregiver can selection the View icon 265 multiple times to cycle through the various view settings. The Split Screen View allows the caregiver to display the main display portion 207 (described below), along with a resuscitation display portion 350, discussed below (See FIG. 3). It will be noted that the various available views may be set initially by a manufacturer or hospital administrator, thus eliminating the need for the caregiver to configure the display prior to operation.

If the caregiver selects the Work Light icon 266, the work light (not shown) associated with the warming therapy device 100 is switched 'on' and 'off.' For example, if the work light is 'on' when the caregiver selects the Work Light icon 266, the light will be turned 'off.' Similarly, if the work light is 'off' when the caregiver selects the Work Light icon 266, the light will be turned 'on.'

If the caregiver selects the Night Light icon 267, the night light (not shown) associated with the warming therapy device 100 is switched 'on' and 'off.' For example, if the night light is 'on' when the caregiver selects the Night Light icon 266, the light will be turned 'off.' Similarly, if the night light is 'off' when the caregiver selects the Night Light icon 266, the light will be turned 'on.'

If the caregiver selects the Bed Adjustment icon 268, a separate dialog box or window is displayed (not shown) which allows the caregiver to manipulate the configuration settings for the warming therapy device (e.g., change the height of the mattress tray assembly 140, tilt the mattress tray assembly, etc.).

If the caregiver selects the Screen Lock icon 269, the screen lock for the GUI 200 is switched 'on' and 'off.' For example, if the screen lock is 'on' when the caregiver selects the Screen Lock icon 269, the lock will be turned 'off.' Similarly, if the screen lock is 'off' when the caregiver selects the Screen Lock icon 269, the lock will be turned 'on.' A graphical indicator (a lock with an open or closed clasp in FIG. 2) shows whether the screen is in the 'locked' or 'unlocked' state. When the screen lock is 'on' all controls on the GUI 200 (except the Screen Lock icon 269, as well as any other vital radio buttons, displays or icons) are either hidden or disabled.

The GUI 200 also includes a main display portion 207 which includes various displays and radio buttons. For example, the main display portion 207 includes a patient monitoring portion 270 which can display information such as: (1) oxygen levels, (2) patient temperature, (3) air temperature, (4) humidity, and (5) mattress temperature. The patient monitoring portion 270 is preferably laid out in a circular or oval pattern as shown in FIG. 2, where various gauges form the periphery of the circle or oval. The gauges around the periphery of the oval pattern show graphical representations of various values, such as air temperature (upper middle), mattress temperature (lower middle), humidity (right side) and oxygen level (left side). Next to each gauge us a numeric representations of the corresponding value. At the center of the oval pattern is a depiction of an infant patient 271, as well as one or more indicators 272 related to one or more probes coupled to the patient (e.g., Skin 1, Skin 2). The references "Skin 1" and "Skin 2" on the patient monitoring portion 270 correspond to probes which are coupled to the skin of the patient to measure temperature. In the exemplary GUI 200 shown in FIG. 2, the skin temperature reading for both probes is 36.5° C. (97.7° F.). Although the temperature reading is shown in FIG. 2 as being in Celsius, the caregiver can configure the format of the temperature displayed by the GUI 200 to Fahrenheit, Kelvin, or any other suitable measure. Preferably, the "Skin 1" probe is the primary temperature probe for the patient, and the indicator 272 associated therewith will read zero (0) if the associated probe is not coupled to the patient's skin. The "Skin 2" probe is a secondary probe that may be selectively displayed on the GUI 200. For example, if the probe associated with the "Skin 2" reference is not coupled to the patient, the "Skin 2" reference may not be displayed on the GUI 200.

The main display portion 207 also includes an air temperature portion 273 which includes "On" and "Off" radio buttons for selectively circulating heated air under the hood 145. The air temperature portion 273 also includes a radio button (e.g., "Set 33.0") for setting the temperature of the circulated air, and a display showing the actual temperature of the air inside the hood 145. As shown in FIG. 2, the air temperature has been set to a temperature of 33.0° C. (91.3° F.), and the actual temperature under the hood 145 is also 33.0° C. (91.3° F.). The air temperature may be measured by a temperature sensor, or equivalent means known in the art, which is coupled to the monitor 150. The air temperature portion 273 also includes a graphical indicator (represented by three wavy lines in FIG. 2) which indicates that air is currently being circulated.

The main display portion 207 also includes a mattress temperature portion 274 which includes a radio button (e.g., "Set 36.5") for setting the temperature of a heated mattress, and a display showing the actual temperature at the mattress. As shown in FIG. 2, the mattress temperature has been set to a temperature of 36.5° C. (97.7° F.), and the actual temperature at the mattress is also 36.5° C. (97.7° F.). The mattress temperature may be measured by a temperature sensor, or equivalent means known in the art, which is coupled to the monitor 150. The mattress temperature portion 274 also includes a graphical indicator (represented by an oval with several wavy lines emanating upward therefrom in FIG. 2) which indicates that heated mattress is currently active.

The main display portion 207 also includes an oxygen level portion 275 which includes a radio button (e.g., "Set 21") for setting the oxygen level, and a display showing the actual oxygen level inside the hood 145. As shown in FIG. 2, the oxygen level has been set to a level of 21, and the actual oxygen level inside the hood 145 is also 21. The oxygen level inside the hood 145 may be measured by an oxygen sensor, or equivalent means known in the art, which is coupled to the monitor 150. The oxygen level portion 275 also includes a graphical indicator (represented by a leaf in FIG. 2) which indicates that oxygen is being supplied to the patient under the hood 145.

Finally, the main display portion 207 includes a humidity level portion 276 which includes a radio button (e.g., "Set 30") for setting the humidity level, and a display showing the actual humidity level inside the hood 145. As shown in FIG. 2, the humidity level has been set to a level of 30, and the actual humidity level inside the hood 145 is also 30. The humidity level inside the hood 145 may be measured by a humidity sensor, or equivalent means known in the art, which is coupled to the monitor 150. The humidity level portion 276 also includes a graphical indicator (represented by raindrops in FIG. 2) which indicates that the humidity control system is enabled.

The main display portion 207 of the GUI 200 also includes a heater power portion 280, a CPAP portion 290, a heart rate portion 300, and a resuscitation portion 310, which will be described below.

The heater power portion 280 includes a radio button in the shape of a thermometer with a (triangular) indicator along one side, and a display showing the heater power (e.g., 25%, 50%, 100%, etc.). The caregiver may touch the radio button to change the power level of the radiant heater head 120. For example, if the caregiver moves the triangular indicator halfway up the thermometer, the radiant heater head 120 will be at approximately 50% power. The heater power portion 280 also includes a graphical indicator (represented by an oval with several straight lines emanating therefrom in FIG. 2) which indicates that the radiant heater head 120 is enabled.

The CPAP portion 290 includes an "On/Off" radio button for selectively displaying a CPAP meter 291. The CPAP meter 291 displays the CPAP level and the PIP level, and may be used for monitoring airway pressure as is known in the art. The ability to display gauges, levels and values associated with CPAP processes on the GUI 200' substantially eliminates the need for one or more separate analog display gauges and meters, as is the case in many conventional warming therapy devices. This, in turn, allows a significant reduction in the overall space requirements for the devices.

The heart rate portion 300 includes an oxygen saturation (SpO2) display and a pulse display. The oxygen saturation display shows the oxygen saturation of the patient's blood in percentage, and the pulse display shows the patient's pulse in beats per minute (bpm). The oxygen saturation and pulse levels of the patient may be measured by either or both of the "Skin 1" and "Skin 2" probes discussed above, or by other means known to those of ordinary skill in the art. The heart rate portion 300 also includes a graphical indicator (represented by a heart in FIG. 2) which indicates that the pulse and oxygenation levels of the patient are presently being monitored.

Figure 3:
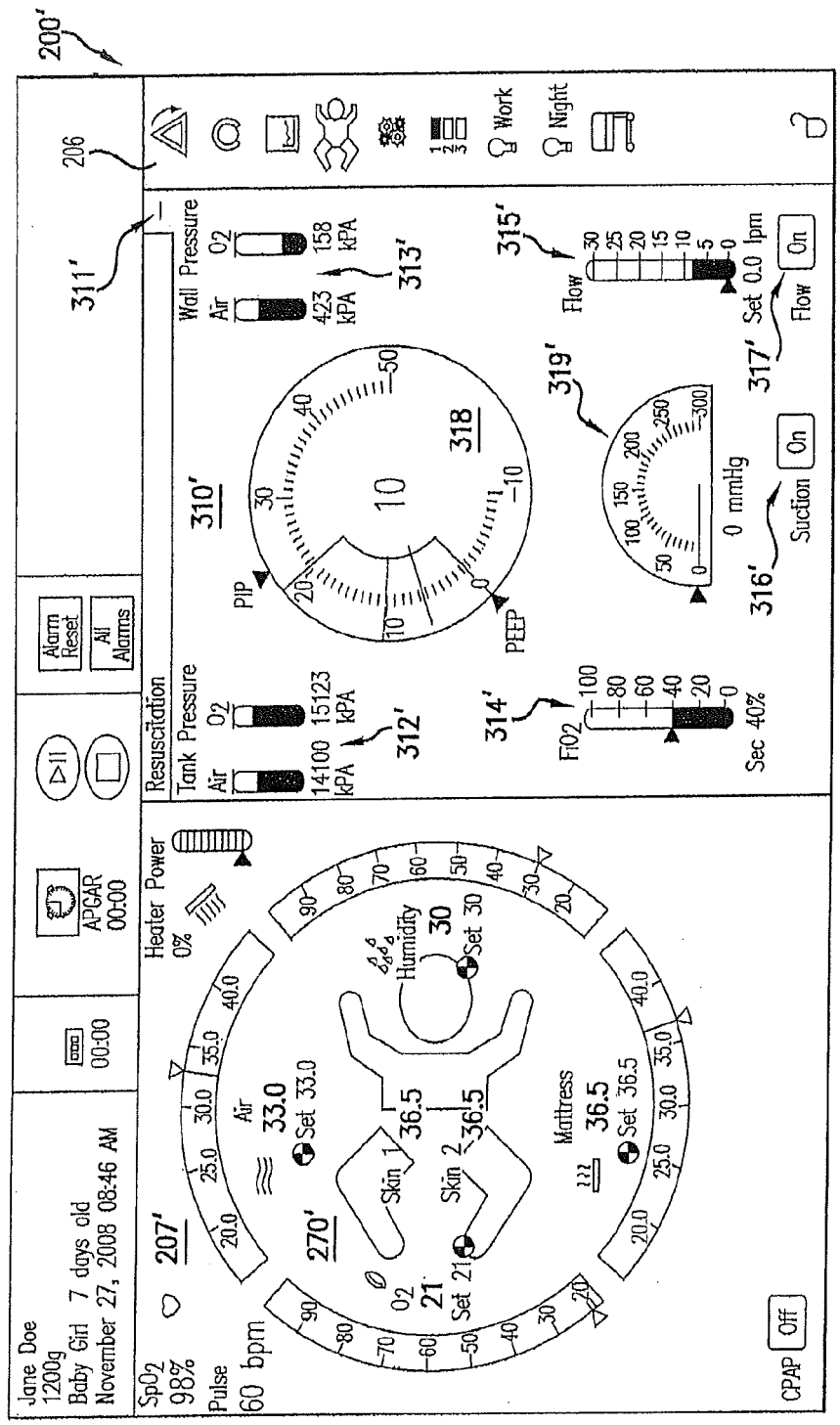
FIG. 3 is an alternative front view of the GUI of FIG. 2, showing the resuscitation portion expanded.

The resuscitation portion 310 is minimized in FIG. 2, and thus no information is shown. Additional information can be shown if the caregiver selects the "Resuscitation" radio button in the resuscitation portion 310, and expands the resuscitation portion. FIG. 3 shows the resuscitation portion 310 expanded, and further details thereon are discussed below.

FIG. 3 shows an alternative view of the GUI 200 which will be referenced as GUI 200'. In particular, FIG. 3 shows the Split Screen View discussed above. The GUI 200' includes many of the same elements as the GUI 200, and like reference numerals denote like elements. One difference is that the main display portion 207' is about half the size of the main display portion 207 shown in FIG. 2, which results in the patient monitoring portion 270' being more circular than oval. The other difference is the presence of the resuscitation portion 310' as part of the main display portion 207'. In particular, the resuscitation portion 310' has been expanded from the minimized position shown in FIG. 2. This may be accomplished by the caregiver touching the resuscitation portion 310 shown in FIG. 2. The resuscitation portion 310' may be minimized again (to the position shown in FIG. 2) by selecting of the 'minus' radio button 311' (the "–" button in FIG. 3). Another difference is that the CPAP portion 290 of the main display portion 207 is not shown in the main display portion 207' shown in FIG. 3. This is because the CPAP portion is alternatively displayed in the resuscitation portion 310', and thus the CPAP portion "On/Off" radio button has been switched to the "Off" position by default.

The resuscitation portion 310' includes a tank pressure display 312', a wall pressure display 313', a FiO2 display 314', and a flow display 315'. The resuscitation portion 310' also includes a suction "On/Off" radio button 316', and a flow "On/Off" radio button 317'. The resuscitation portion 310' also includes a CPAP meter 318' and a blood pressure meter 319'. The tank pressure display 312' displays the pressure for one or more gas tanks (e.g., Air and Oxygen) in kilopascals (kPa). The wall pressure display 313' displays the wall pressure for one or more gas tanks (e.g., Air and Oxygen) in kilopascals (kPa). The FiO2 display 314' displays the FiO2 concentration as a percentage (e.g., 40% as shown in FIG. 3). The flow display 315' displays the gas flow rate in liters per minute (lpm). As noted above with regard to the CPAP portion 290, the ability to display gauges, levels and values associated with resuscitation processes on the GUI 200' substantially eliminates the need for one or more separate analog display gauges and meters, as is the case in many conventional warming therapy devices. This, in turn, allows a significant reduction in the overall space requirements for the devices.

Figure 4:
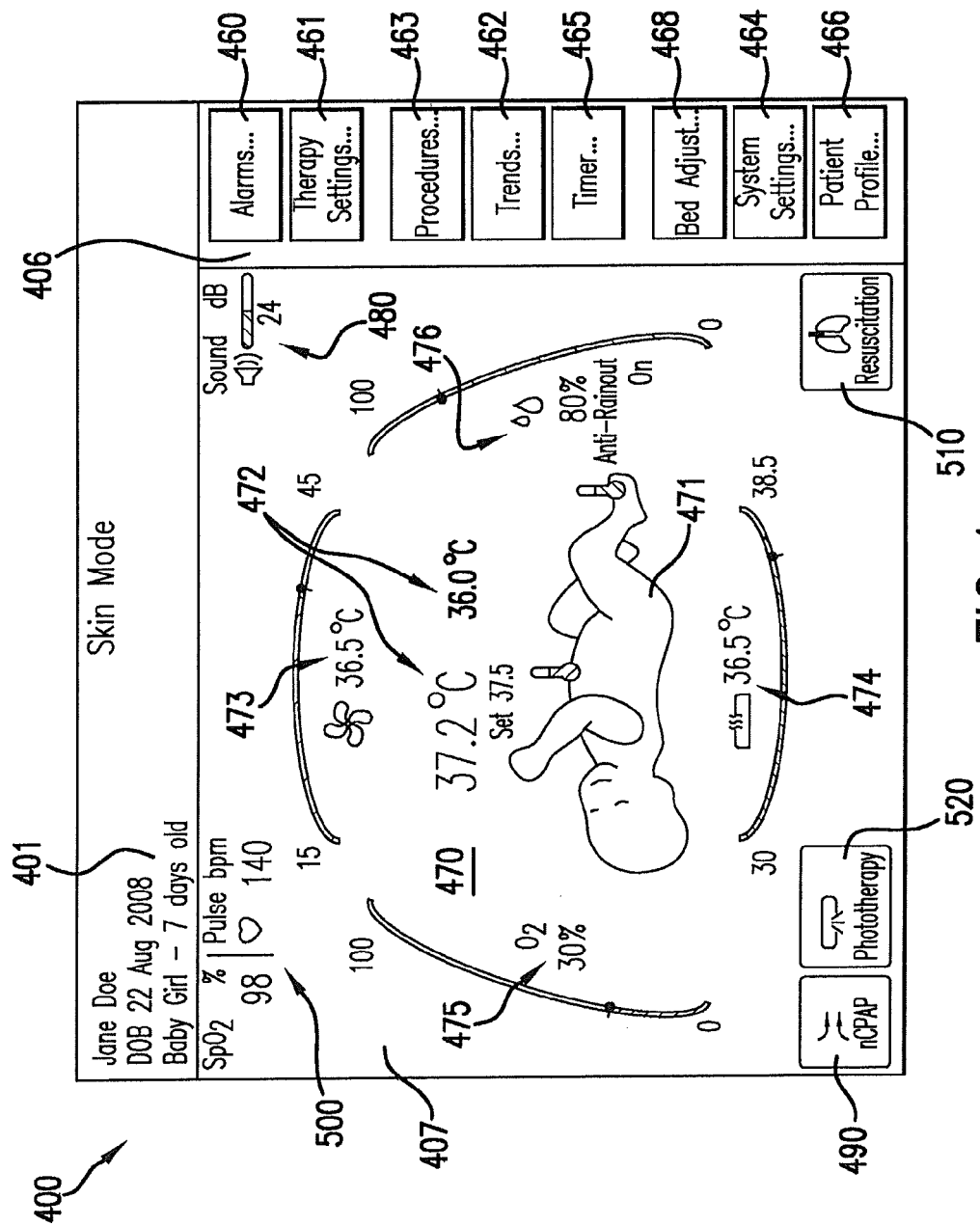
FIG. 4 is front view of a computer monitor associated with the warming therapy device shown in FIG. 1, showing a touch screen Graphical User Interface (GUI) according to a second exemplary embodiment of the present invention.

FIG. 4 shows a Graphical User Interface (GUI) 400 according to a second exemplary embodiment of the present invention which may be displayed on the monitor 150 discussed above. The GUI 400 is similar to the GUI 200 discussed above, and like reference numerals denote like elements. In the second exemplary embodiment, the GUI 400 comprises a 'touch screen' (as is known in the art) which is capable of receiving input from a user (e.g., caregiver) by the user touching various portions of a monitor (e.g., monitor 150) associated with the GUI.

The GUI 400 includes a patient information portion 401, which can display various personal information associated with the patient, such as name, weight, sex, and age. Although not shown, the patient information portion 401 can also display the current date and time for reference purposes, and a battery level indicator.

The GUI 400 also includes a main menu portion 406 for allowing the caregiver to perform various functions. The main menu portion 406 includes an Alarm icon 460, a Therapy Settings icon 461, a Trends/Review icon 462, a Procedures icon 463, a System Setup icon 464, a Timer icon 465 (that allows a user to configure a general purpose timer), a Bed Adjustment icon 468, and a Patient Profile icon 466 (that allows a user to enter Admit, Discharge and/or Transfer information pertaining to the patient). Although not shown in FIG. 4, the main menu portion 206 may include additional icons for performing additional functions, such as, a Hood icon for opening and closing the hood 145, a Tilt icon for tilting the mattress tray assembly 140, and a Help icon for accessing help information for the GUI.

If the caregiver selects the Alarm icon 460, a separate dialog box or window is displayed (not shown) which allows the caregiver to manipulate the alarm settings (e.g., which alarms are active, audio options, etc.). This dialog box (and all the other dialog boxes described below) may be configured to disappear or be removed from the GUI 200 if there is no activity in the GUI for a certain period of time (e.g., 5 seconds). Controls available from the Alarm dialog box may include radio buttons, softkeys or other equivalent means for controlling various alarms related to conditions such as patient temperature, mattress temperature, oxygen levels, humidity levels, etc. The Alarm dialog box may also permit the disabling of all alarms, the display of all current alarms and alarm levels, the display of historical alarms and alarm levels and alarm volume controls.

If the caregiver selects the Therapy Settings icon 461, a separate dialog box or window is displayed (not shown) which allows the caregiver to manipulate the therapy settings (e.g., mattress heating, heated air circulation, resuscitation settings, etc.). Controls available from the Therapy Settings dialog box may include radio buttons, softkeys or other equivalent means for controlling temperature, air flow and humidity within the warming therapy device, mattress temperature, radiant heater temperature, oxygen levels, resuscitation processes, and nCPAP processes. The Therapy Settings dialog box may also permit the enabling or disabling of a Kangaroo Mode®, wherein a parent or caregiver removes the medical patient from the warming therapy device but remains in close proximity.

If the caregiver selects the Trends/Review icon 462, a separate dialog box or window is displayed (not shown) which allows the caregiver to manipulate the trends and review settings (e.g., select trends to monitor, display trends, display current values, etc.). Controls available from the Trends/Review dialog box may include radio buttons, softkeys or other equivalent means for displaying various trends.

If the caregiver selects the Procedures icon 463, a separate dialog box or window is displayed (not shown) which allows the caregiver to manipulate the procedures settings (e.g., weight measurements, phototherapy procedures, etc.). Controls available from the Procedures dialog box may include radio buttons, softkeys or other equivalent means for performing various procedures such as weighing the patient, performing phototherapy on the patient (to reduce or eliminate bilirubin), and performing audio stimulation (e.g., playing music or soothing sounds for the patient). The Procedures dialog box may also permit the setting of various timers for the above-referenced procedures.

If the caregiver selects the System Setup icon 464, a separate dialog box or window is displayed (not shown) which allows the caregiver to manipulate the system settings (e.g., screen settings, trend settings, view settings, color settings, alarm settings, etc.). Controls available from the System Setup dialog box may include radio buttons, softkeys or other equivalent means for controlling current date and time, language, display brightness, display and editing of patient demographic information, enabling or disabling APGAR displays and controls, setting of units of measurement (e.g., ounces, pounds, kilograms, etc.), enabling or disabling locking of the touch screen, and enabling or disabling tilt and height adjustment controls. The System Setup dialog box may also permit control of trend default levels (e.g., for display in the Trends/Review dialog box), defaults views (e.g., for display in the View dialog box), default alarms and levels (e.g., for display in the Alarm dialog box), and default therapies and levels (e.g., for display in the Therapy Settings dialog box). The System Setup dialog box may also permit the assignment of various colors to different parameters, to make on-screen identification easier. For example, the caregiver may assign the color red to a patient temperature display, and the color blue to an oxygen level display. The System Setup dialog box may also permit the saving of data to an external data storage medium (e.g., Universal Serial Bus (USB) Drive, or the like), and the loading of data from an external data storage medium. The System Setup dialog box may also permit calibration of the oxygen sensors.

If the caregiver selects the Timer icon 465, a separate dialog box or window is displayed (not shown) which allows the caregiver to configure and engage a general purpose timer. Controls available from the System Setup dialog box may include radio buttons, softkeys or other equivalent means for entering a start time for the countdown timer, starting the timer, and stopping the timer. For various applications, such as 'Kangaroo Care' (i.e., wherein a parent or caregiver removes the medical patient from the warming therapy device but remains in close proximity), APGAR assessment, resuscitation, feeding, etc. it is necessary to closely monitor the time when the activity was started. Depending on the user's preference, the timer may comprise a countdown timer or a timer starting at zero (0) and counting up.

If the caregiver selects the Patient Profile icon 466, a separate dialog box or window is displayed (not shown) which allows the caregiver to enter Admit, Discharge and/or Transfer information pertaining to the patient. Controls available from the System Setup dialog box may include radio buttons, softkeys or other equivalent means for entering patient name, age, gender, race, birth date, etc.

If the caregiver selects the Bed Adjustment icon 468, a separate dialog box or window is displayed (not shown) which allows the caregiver to manipulate the configuration settings for the warming therapy device (e.g., change the height of the mattress tray assembly 140, tilt the mattress tray assembly, etc.). Controls available from the System Setup dialog box may include radio buttons, softkeys or other equivalent means for adjusting bed height and tilt, and adjusting hood height and tilt.

The GUI 400 also includes a main display portion 407 which includes various displays and radio buttons. For example, the main display portion 407 includes a patient monitoring portion 470 which can display information such as: (1) oxygen levels, (2) patient temperature, (3) air temperature, (4) humidity, and (5) mattress temperature. The patient monitoring portion 470 is preferably laid out in a circular or oval pattern as shown in FIG. 4, where various gauges form the periphery of the circle or oval. The gauges around the periphery of the oval pattern show graphical representations of various values, such as air temperature (upper middle), mattress temperature (lower middle), humidity (right side) and oxygen level (left side). Next to each gauge us a numeric representations of the corresponding value. At the center of the oval pattern is a depiction of an infant patient 471, as well as one or more patient temperature indicators 472. The temperature indicators 472 indicate the temperature at different portions of the patient, such as for example, the torso and the feet. In the exemplary GUI 400 shown in FIG. 4, the temperature reading for the torso region is 37.2° C. (98.96° F.), and the temperature reading for the feet region is 36.0° C. (96.8° F.). Although the temperature reading is shown in FIG. 4 as being in Celsius, the caregiver can configure the format of the temperature displayed by the GUI 400 to Fahrenheit, Kelvin, or any other suitable measure.

The main display portion 407 also includes an air temperature portion 473 which includes a display showing the actual temperature of the air inside the hood of the warming therapy device (e.g., hood 145 in device 100 shown in FIG. 1). The air temperature may be measured by a temperature sensor, or equivalent means known in the art, which is coupled to the monitor 150. The air temperature portion 473 may also include a graphical indicator (represented by fan blades in FIG. 4) which indicates whether air is currently being circulated.

The main display portion 407 also includes a mattress temperature portion 474 which includes a display showing the actual temperature at the mattress (e.g., mattress 111 in FIG. 1). As shown in FIG. 4, the actual temperature at the mattress is 36.5° C. (97.7° F.). The mattress temperature may be measured by a temperature sensor, or equivalent means known in the art, which is coupled to the monitor 150. The mattress temperature portion 274 may also include a graphical indicator (represented by a rectangle with several wavy lines emanating upward therefrom in FIG. 4) which indicates whether heating of the mattress is currently occurring.

The main display portion 407 also includes an oxygen level portion 475 which includes a display showing the actual oxygen level inside the warming therapy device (e.g., hood 145 in device 100 shown in FIG. 1). As shown in FIG. 4, the measured oxygen level is 30%. The oxygen level may be measured by an oxygen sensor, or equivalent means known in the art, which is coupled to the monitor 150. The oxygen level portion 275 may also include a graphical indicator (not shown) which indicates that oxygen is being supplied to the patient.

Finally, the main display portion 407 includes a humidity level portion 476 which includes a display showing the actual humidity level inside the warming therapy device (e.g., hood 145 in device 100 shown in FIG. 1). As shown in FIG. 4, the measured humidity level is 80%. The humidity level may be measured by a humidity sensor, or equivalent means known in the art, which is coupled to the monitor 150. The humidity level portion 476 may also include a graphical indicator (represented by raindrops in FIG. 4) which indicates that the humidity control system is enabled. The humidity level portion 476 of the main display portion 407 may also include a radio button, softkey or other equivalent means for selecting a "Condensation Management" or "Anti-Rainout" protocol. When the protocol is engaged or 'on' (as shown in FIG. 4), the humidity within the hood is controlled so as to substantially prevent condensation from forming For example, when the humidity level is set at high levels, such as ninety-five percent (95%) relative humidity, there is a high likelihood (depending on the room temperature) that condensation inside the walls of the warming therapy device will be so intense that the infant patient inside the incubator cannot be seen from the outside. Additionally, high humidity levels and interior condensation 'swamp' the inside of the warming therapy device, and increase the risk of infection. The protocol operates to substantially prevent such an occurrence.

The main display portion 407 of the GUI 400 also includes a volume control portion 480, a nCPAP portion 490, a heart rate portion 500, a resuscitation portion 510, and a phototherapy portion 520, which will be described below.

The volume control portion 480 includes a display showing the current volume level (e.g, 24). The caregiver may touch the volume control portion to change the volume level, or mute the volume level. For example, the caregiver may slide their finger across the volume control portion 480 from left to right to raise the volume level, and from right to left to lower the volume level. The volume control portion 480 also includes a graphical indicator (represented by a speaker with sound waves emanating therefrom in FIG. 4) which indicates whether sound is enabled. If sound is not enabled (or if sound has been muted), this graphical indicator may take the form of a speaker with a line through it, as is well known in the art.

Figure 5:
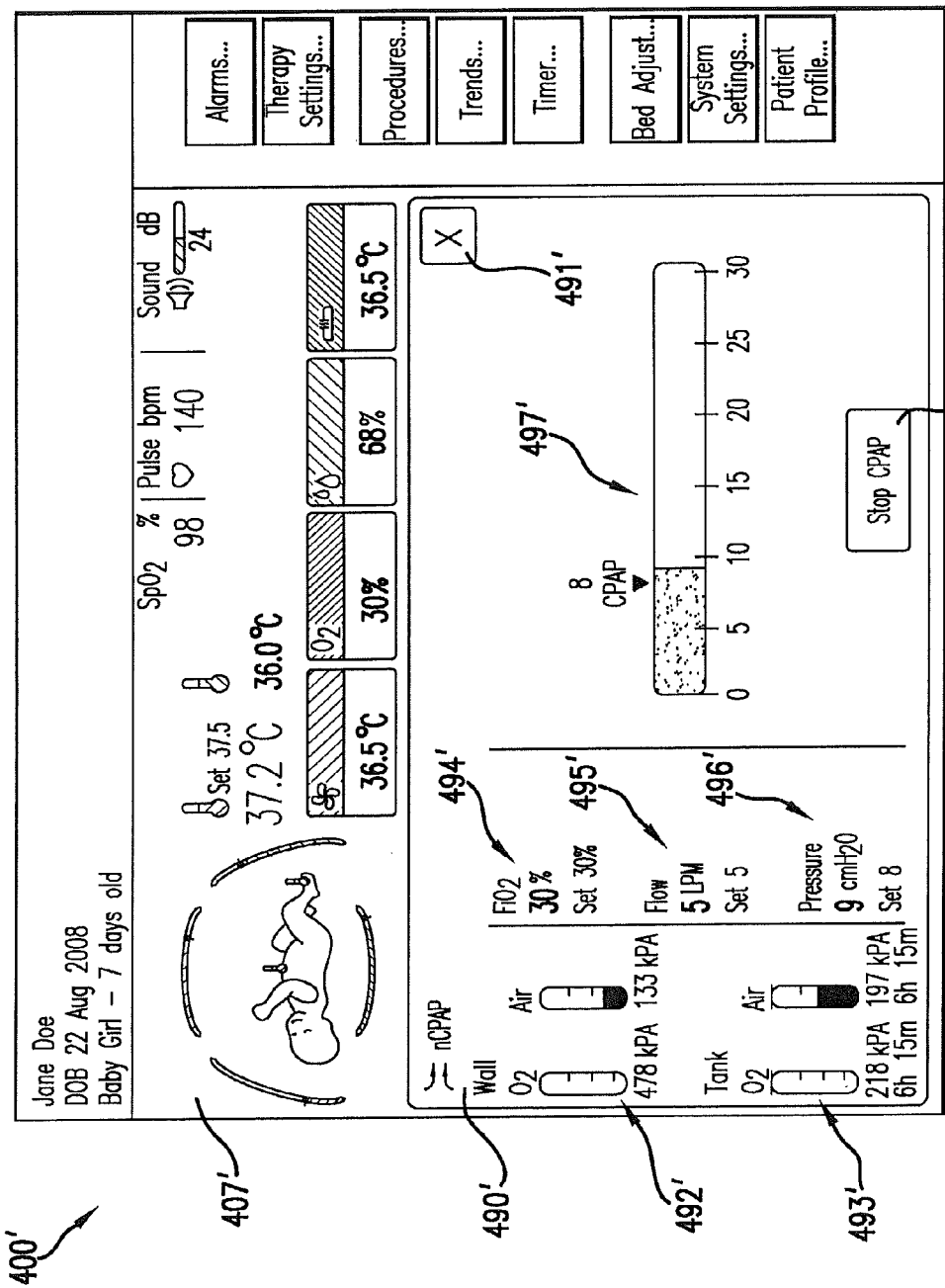
FIG. 5 is an alternative front view of the GUI of FIG. 4, showing the nCPAP portion expanded.
Figure 6:
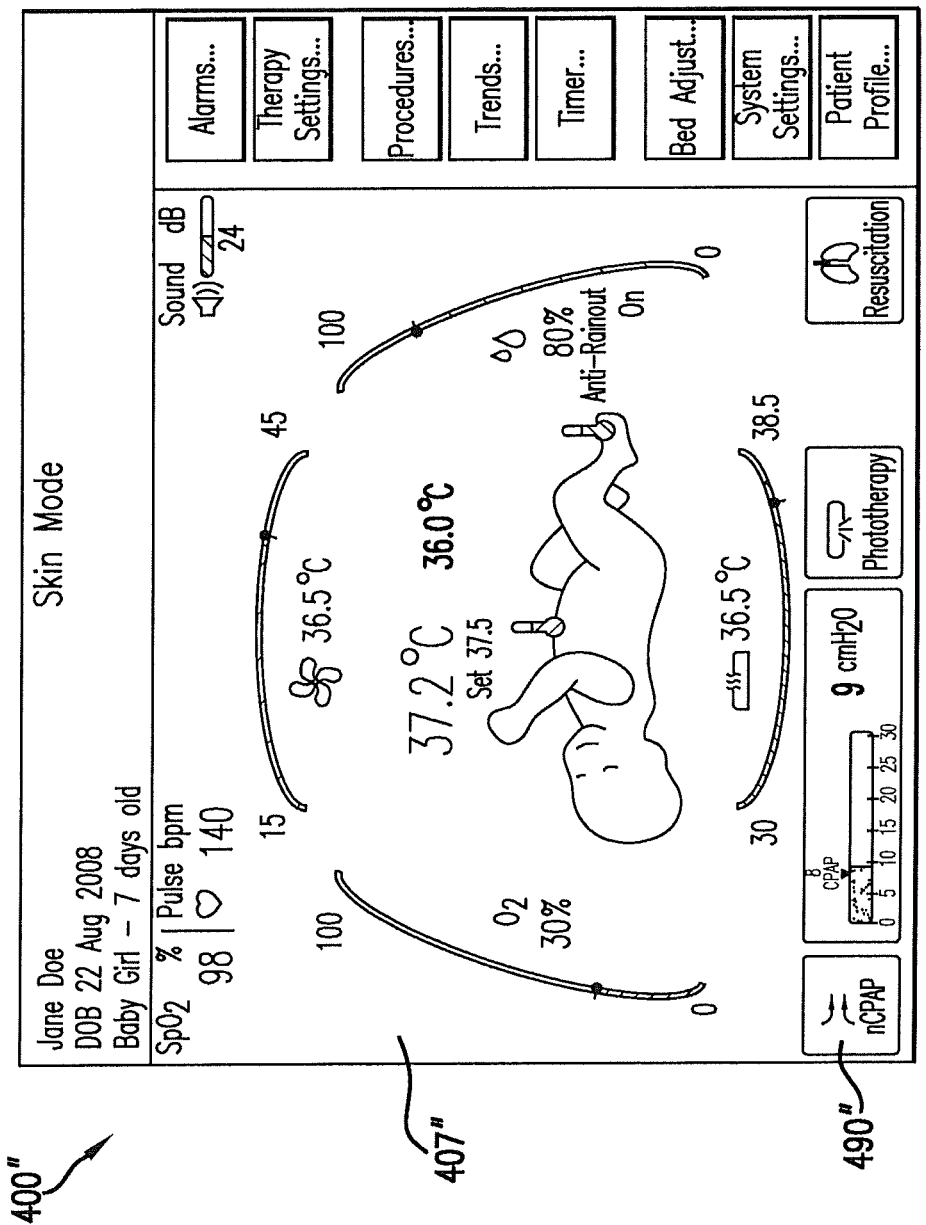
FIG. 6 is an alternative front view of the GUI of FIG. 4, showing the nCPAP portion expanded.

The nCPAP portion 490 includes a radio button for selectively displaying additional nCPAP information. For example, selection of the radio button may expand the nCPAP portion 490, and correspondingly minimize other portions of the GUI 400, as shown in FIGS. 5 and 6. Further details of the nCPAP portion 490 are provided below.

The heart rate portion 500 includes an oxygen saturation (SpO2) display and a pulse display. The oxygen saturation display shows the oxygen saturation of the patient's blood in percentage, and the pulse display shows the patient's pulse in beats per minute (bpm). The oxygen saturation and pulse levels of the patient may be measured by means known to those of ordinary skill in the art. The heart rate portion 500 also includes a graphical indicator (represented by a heart in FIG. 4) which indicates that the pulse and oxygenation levels of the patient are presently being monitored.

Figure 7:
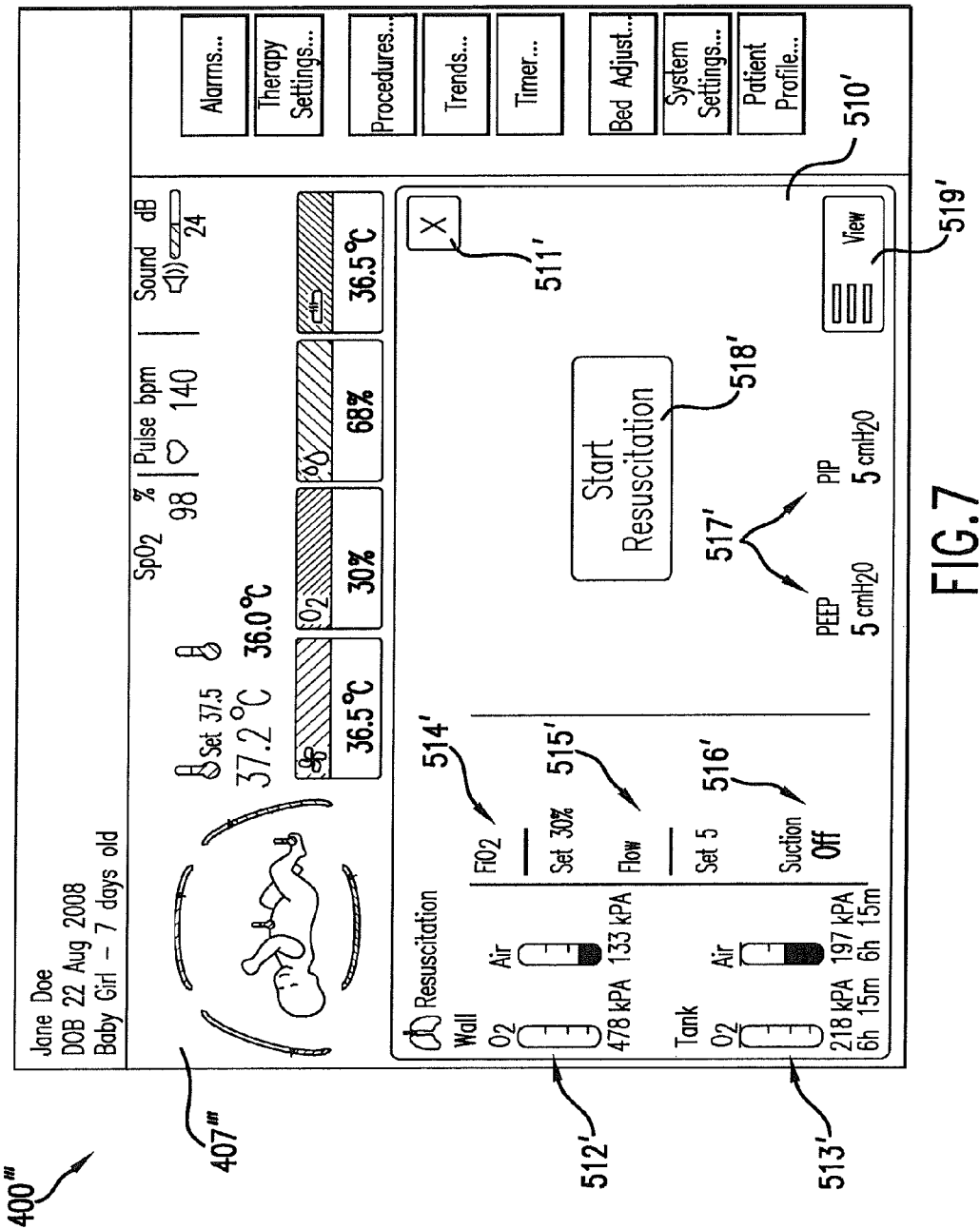
FIG. 7 is an alternative front view of the GUI of FIG. 4, showing the resuscitation portion expanded.
Figure 8:
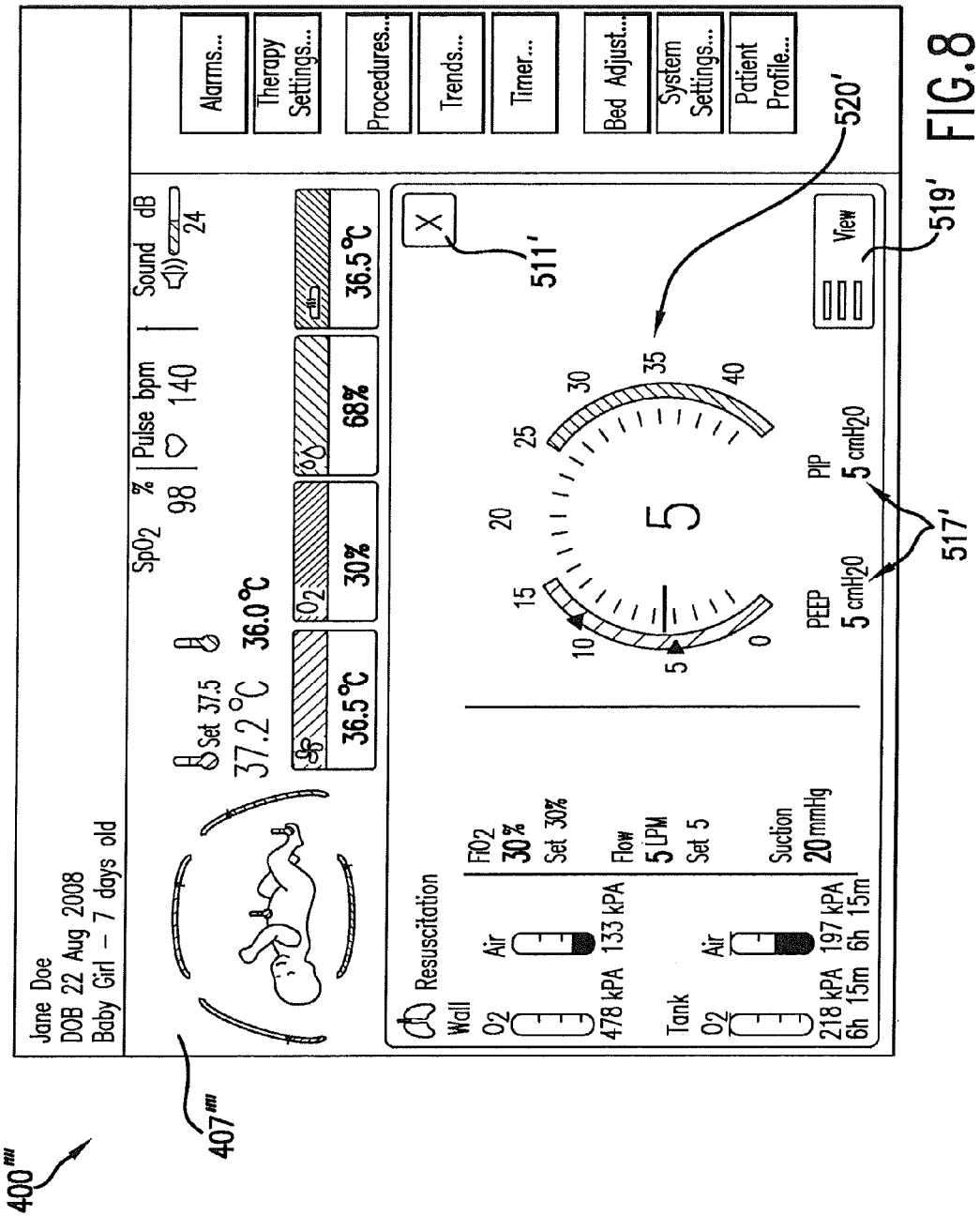
FIG. 8 is an alternative front view of the GUI of FIG. 4, showing the resuscitation portion expanded.

The resuscitation portion 510 includes a radio button for selectively displaying additional resuscitation information. For example, selection of the radio button may expand the resuscitation portion 510, and correspondingly minimize other portions of the GUI 400, as shown in FIGS. 7 and 8. Further details of the resuscitation portion 510 are provided below.

The phototherapy portion 520 includes a radio button for selectively displaying additional phototherapy information. For example, selection of the radio button may expand the phototherapy portion 520, and correspondingly minimize other portions of the GUI 400 (not shown, but similar to the displays shown in FIGS. 5-8). Further details of the phototherapy portion 520 are provided below.

FIG. 5 shows a first alternative view of the GUI 400 which will be referenced as GUI 400'. The GUI 400' includes many of the same elements as the GUI 400, and like reference numerals denote like elements. One difference is that the main display portion 407' is about half the size of the main display portion 407 shown in FIG. 4. The other difference is the enlarged nCPAP portion 490'. As noted above, enlargement of the nCPAP portion 490' may be accomplished by the caregiver touching the nCPAP portion 490 shown in FIG. 4. The nCPAP portion 490' may be minimized again (to the position shown in FIG. 4) by selection of the 'X' radio button 491' in FIG. 5. When enlarged as shown in FIG. 5, the nCPAP portion 490' includes wall oxygen and air supply pressure monitors 492', tank oxygen and air supply pressure monitors 493'. The nCPAP portion 490' also includes a FiO2 portion 494', a flow portion 495', and a pressure portion 496'. Also shown is a CPAP level indicator 497', and a 'Stop CPAP' radio button 498'. The FiO2 portion 494' allows the user to adjust the FiO2 set point, the flow portion 495' allows the user to adjust the flow set point, and the pressure portion 496' allows the user to adjust the pressure set point. Similarly, the CPAP level indicator 497' allows the user to adjust the CPAP set point, and the 'Stop CPAP' radio button 498' toggles CPAP between 'on' and 'off' states. The ability to display gauges, levels and values associated with CPAP processes on the GUI 400' substantially eliminates the need for one or more separate analog display gauges and meters, as is the case in many conventional warming therapy devices. This, in turn, allows a significant reduction in the overall space requirements for the devices.

FIG. 6 shows a second alternative view of the GUI 400 which will be referenced as GUI 400". The GUI 400" includes many of the same elements as the GUI 400, and like reference numerals denote like elements. One difference is that the main display portion 407" is slightly smaller than the main display portion 407 shown in FIG. 4. The other difference is the enlarged nCPAP portion 490". As noted above, enlargement of the nCPAP portion 490" may be accomplished by the caregiver touching the nCPAP portion 490 shown in FIG. 4. The version of the nCPAP portion 490" shown in FIG. 6 is displayed when nCPAP therapy is initiated in FIG. 5, and then nCPAP information is minimized by selecting the 'X' radio button shown in the upper right hand corner of the nCPAP portion 490' in FIG. 5.

FIG. 7 shows a third alternative view of the GUI 400 which will be referenced as GUI 400'''. The GUI 400''' includes many of the same elements as the GUI 400, and like reference numerals denote like elements. One difference is that the main display portion 407''' is about half the size of the main display portion 407 shown in FIG. 4. The other difference is the enlarged resuscitation portion 510'. As noted above, enlargement of the resuscitation portion 510' may be accomplished by the caregiver touching the resuscitation portion 510 shown in FIG. 4. The resuscitation portion 510' may be minimized again (to the position shown in FIG. 4) by selection of the 'X' radio button 511' in FIG. 7. When enlarged as shown in FIG. 7, the resuscitation portion 510' includes wall oxygen and air monitors 512', tank oxygen and air monitors 513'. The resuscitation portion 510' also includes a FiO2 portion 514', a flow portion 515', and a suction portion 516'. Also shown are resuscitation level indicators 517', a 'Start Resuscitation' radio button 518', and a 'View' radio button 519'. The FiO2 portion 514' allows the user to adjust the FiO2 set point, the flow portion 515' allows the user to adjust the flow set point, and the suction portion 516' allows the user to toggle suction between 'on' and 'off' states. Similarly, the PEEP and PIP resuscitation level indicators 517' allow the user to adjust the PEEP and PIP set points, and the 'Start Resuscitation' radio button 518' allows the user to toggle resuscitation between 'on' and 'off' states. The 'View' radio button 519' permits the view shown on the GUI 400 to be changed between different formats. As discussed above, exemplary views may include: (1) a Portrait View (7.2-8.4 inches wide by 9.6-11.2 inches high), (2) a Landscape View (9.6-11.2 inches wide by 7.2-8.4 inches high), and (3) a Split Screen View (two screens side by side with each being 4.5 inches wide by 3.25 inches high). The ability to display gauges, levels and values associated with resuscitation processes on the GUI 400' substantially eliminates the need for one or more separate analog display gauges and meters, as is the case in many conventional warming therapy devices. This, in turn, allows a significant reduction in the overall space requirements for the devices.

FIG. 8 shows a fourth alternative view of the GUI 400 which will be referenced as GUI 400''''. The GUI 400'''' includes many of the same elements as the GUI 400, and like reference numerals denote like elements. One difference between the GUI 400''' shown in FIG. 7 and the GUI 400'''' shown in FIG. 8 is the presence of a resuscitation display 520'. As noted above, the resuscitation display 520' may be presented to the caregiver when the caregiver selects the 'Start Resuscitation' radio button 518' shown in FIG. 7. The resuscitation display 520' may include a circular dial including visual indicators showing the PEEP and PIP levels displayed by the resuscitation level indicators 517'.

Although exemplary embodiments of the present invention have been described above for use in procedures involving infants, those of ordinary skill in the art will realize that the exemplary embodiments of the present invention may be used for other types of operations and procedures, including for children and adults.

Although the invention has been described in terms of exemplary embodiments, it is not limited thereto. Rather, the appended claims should be construed broadly to include other variants and embodiments of the invention which may be made by those skilled in the art without departing from the scope and range of equivalents of the invention. This disclosure is intended to cover any adaptations or variations of the embodiments discussed herein.

What is claimed is:

1. An apparatus comprising:
 a monitor; and
 a computer processor coupled to the monitor and configured to generate a graphical user interface on the monitor comprising a first display portion configured to display a first set of information related to a medical patient, wherein the first display portion comprises:
   a first information portion comprising a substantially circular display and including a plurality of sections, wherein each of the plurality of sections are configured to display a value of a parameter related to the medical patient's environment selected from the group consisting of: mattress temperature, air temperature, air circulation, oxygen level and humidity, and a second information portion comprising a human model representative of the medical patient, wherein the second information portion is configured to display one or more physiological measurements of the medical patient, and wherein the second information portion is disposed substantially centrally within the first information portion.

2. The apparatus of claim 1, further comprising:
a second display portion configured to display a second set of information related to the medical patient.

3. The apparatus of claim 2, wherein the second display portion displays medical patient name information.

4. The apparatus of claim 1, further comprising:
a third display portion configured to display menu information.

5. The apparatus of claim 3, further comprising:
a fourth display portion for displaying CPAP information.

6. The apparatus of claim 3, further comprising:
a fourth display portion for displaying resuscitation information.

7. The apparatus of claim 1, further comprising:
a second display portion for displaying CPAP information.

8. The apparatus of claim 1, further comprising:
a second display portion for displaying resuscitation information.

9. The apparatus of claim 1, wherein at least one of the one or more physiological measurements of the medical patient comprises a skin temperature measurement.

10. The apparatus of claim 1, further comprising a warming therapy device.

11. The apparatus of claim 10, wherein the warming therapy device is coupled to the computer processor and the monitor.

12. The apparatus of claim 1, wherein said monitor is removable.

13. A method for monitoring a medical patient, the method comprising:
displaying a first set of information related to the medical patient on a first portion of a computer monitor, wherein the first portion includes:
a first information portion comprising a substantially circular display including a plurality of sections, wherein each of the plurality of sections are configured to display a value of a parameter related to the medical patient's environment selected from the group consisting of: mattress temperature, air temperature, air circulation, oxygen level and humidity, and
a second information portion comprising a human model representative of the medical patient, wherein the second information portion is configured to display one or more physiological measurements of the medical patient, and wherein the second information portion is disposed substantially centrally within the first information portion.

14. The method of claim 13, comprising the further step of:
displaying a second set of information related to a the medical patient on a second portion of the computer monitor.

15. The method of claim 14, wherein the step of displaying a second set of information related to a medical patient comprises displaying medical patient name information.

16. The method of claim 13, comprising the further step of:
displaying menu information on a third portion of the computer monitor.

17. The method of claim 13, wherein at least one of the one or more physiological measurements of the medical patient comprises a skin temperature measurement.

18. An apparatus comprising:
a monitor; and
a computer processor coupled to the monitor and configured to generate a graphical user interface on the monitor comprising a first display portion configured to display a first set of information related to a medical patient, wherein the first display portion comprises:
a first information portion comprising a substantially circular display and including a plurality of sections, wherein each of the plurality of sections are configured to display a value of a parameter related to the medical patient's environment selected from the group consisting of: mattress temperature, air temperature, air circulation, oxygen level and humidity, and
a second information portion comprising a human model representative of the medical patient, wherein a second portion is configured to display one or more physiological measurements of the medical patient.

19. A method for monitoring a medical patient, the method comprising:
displaying a first set of information related to the medical patient on a first portion of a computer monitor, wherein the first portion includes:
a first information portion comprising a substantially circular display including a plurality of sections, wherein each of the plurality of sections are configured to display a value of a parameter related to the medical patient's environment selected from the group consisting of: mattress temperature, air temperature, air circulation, oxygen level and humidity, and
a second information portion comprising a human model representative of the medical patient, wherein a second portion is configured to display one or more physiological measurements of the medical patient.

* * * * *